(12) United States Patent
Chang et al.

(10) Patent No.: US 6,423,023 B1
(45) Date of Patent: Jul. 23, 2002

(54) METHOD AND APPARATUS FOR ENHANCED PLASMAPHERESIS

(76) Inventors: Yu-An Chang, 3631 Hamilton St., Irvine, CA (US) 92614; Daniel H. Duff, 4851 Barkwood, Irvine, CA (US) 92604; Hosheng Tu, 2151 Palermo, Tustin, CA (US) 92782

( * ) Notice: Subject to any disclaimer, the term of this patent is extended or adjusted under 35 U.S.C. 154(b) by 0 days.

(21) Appl. No.: 09/496,613

(22) Filed: Feb. 2, 2000

(51) Int. Cl.[7] .................. A61M 37/00; B01D 33/00; B01D 24/28

(52) U.S. Cl. ............... 604/6.04; 604/6.09; 210/359; 210/385; 210/780

(58) Field of Search .................. 210/637, 651, 210/247, 780–782, 209, 297, 385, 359, 107, 109, 321.87, 645, 767, 490, 483, 494, 360.1, 787; 604/6.04, 6.09

(56) References Cited

U.S. PATENT DOCUMENTS

| 4,191,182 A | 3/1980 | Popovich et al. ........ 128/214 R |
| 4,212,742 A | 7/1980 | Solomon et al. ............ 210/247 |
| 4,735,726 A | 4/1988 | Duggins ..................... 210/637 |
| 5,034,135 A | 7/1991 | Fischel ........................ 210/651 |
| 5,194,145 A | 3/1993 | Schoendorfer ............... 210/90 |
| 5,234,608 A | 8/1993 | Duff ........................... 210/806 |
| 5,376,263 A | * 12/1994 | Fischel et al. ................ 210/87 |
| 5,529,691 A | 6/1996 | Brown ..................... 210/512.1 |

* cited by examiner

Primary Examiner—Angela D. Sykes
Assistant Examiner—Leslie R. Deak (57) ABSTRACT

An apparatus and methods for enhanced plasmapheresis comprising a filter membrane under an orbital motion or movement that has optimal local shear forces and maximum plasma flow output. The separation apparatus comprises a first plate, a second plate and a hollow interior therebetween, wherein the second plate is detachably coupled to a non-rotational drive structure that controls the second plate in an orbital motion in reference to a center axis of the first plate for enhanced blood separation.

20 Claims, 4 Drawing Sheets

METHOD AND APPARATUS FOR ENHANCED PLASMAPHERESIS

TECHNICAL FIELD OF THE INVENTION

The present invention generally relates to medical apparatus and methods for separating a suspension of plasma alone and/or with platelets from whole blood. More particularly, the invention relates to an apparatus and methods for enhanced plasmapheresis comprising a filter membrane under an orbital motion that has optimal local shear forces and maximum plasma flow output.

BACKGROUND OF THE INVENTION

Separation of blood into a plasma fraction and a cellular component fraction is desirable for many medical reasons. For example, separation of blood into plasma fractions and cellular component fractions provides for a collection of plasma alone, with the cellular component being returned to the donor with an optional suitable portion of replacement fluid. Thus continuous plasmapheresis provides for the collection of plasma from donors without the removal of the cellular components of the blood. Plasma donation from a patient or donor is generally allowed about twice a week whereas the whole blood donation is allowed once in every two months. Secondly, continuous plasmapheresis can be used therapeutically to remove pathologic substances contained in the plasma portion of the blood, as disclosed by Popovich et al. in U.S. Pat. No. 4,191,182. This can be accomplished by separating the cellular components from the diseased plasma and returning the cellular components to the patient in admixture with a suitable replacement fluid, or by further fractionating the patient's plasma to remove the unwanted substances and returning a major portion of the patient's plasma with the cellular components.

The separation of blood into cellular component fractions and plasma fractions has inherently some difficulties and complications. A brief discussion of the makeup of blood is shown herein for illustration purposes. Approximately 45% of the volume of blood is in the form of cellular components. These cellular components include red cells, white cells and platelets. If cellular components are not handled correctly, the cells may lose their functionality and become useless. Plasma makes up the remaining 55% of the volume of blood. Basically, plasma is the fluid portion of the blood which suspends the cells and comprises a solution of approximately 90% water, 7% protein and 3% of various other organic and inorganic solutes. As used herein, the term "plasmapheresis" refers to the separation of a portion of the plasma fraction of the blood from the cellular components thereof Ultrafiltration has been widely used on a batch-type or continuous basis as a substitute for, or in combination with, dialysis methods in artificial kidneys and the like. In any plasmapheresis-type process effected by ultrafiltration there are various problems which occur during the fractionating of the blood by passing it in a parallel flow pattern over a membrane surface, with a transmembrane pressure sufficient to push the plasma portion of the blood therethrough, while allowing the cellular component portion of the blood to remain thereon. One of these problems is that the flow rates must be controlled fairly closely. Thus, if the flow rate employed is too fast at any moment or at any specific region, detrimental turbulence may occur and excess shear force may cause unwanted hemolysis resulting in general destruction of cellular components. On the other hand, if the flow rate and the transmembrane pressure are not controlled adequately the cellular and macromolecular components of the blood will tend to clog up the membrane thus significantly slowing the ultrafiltration rate. Such clogging can also cause hemolysis to occur.

Along the blood flow route in a plasmapheresis apparatus, plasma continues to pass through the filter membrane while cellular component remains in the blood stream. At the downstream region of the separation process, the blood becomes more viscous and the separation efficiency decreases drastically. This fouling effect or "concentration polarization" phenomenon becomes obvious in a conventional batch-wise or continuous ultrafiltration process. For example, U.S. Pat. No. 3,705,100 to Blatt et al., issued Dec. 5, 1972, discloses a process and apparatus for a blood fractionating process on a batch basis. Furthermore, U.S. Pat. No. 4,191,182 to Popovich et al., issued Mar. 4, 1980, discloses a means for continuous plasmapheresis including a blood input pumping means and a plasma outflow pumping means. Though the average flow rate of the disclosed device is within the non-hemolysis range, the local flow rate and its shear force at any moment and/or at any specific region of the filter membrane may not be adequate to effect the most efficient plasmapheresis. Concentration polarization usually occurs at a later stage in a batch plasmapheresis or at a downstream region in a continuous plasmapheresis.

To compensate for the concentration polarization drawbacks, Solomon et al. in U.S. Pat. No. 4,212,742 discloses a filtration device employing a microporous filtration membrane. The filtration flow channels along the surface of the upstream side of the membrane wall are provided with gradually and uniformly increases from the inlet end to the outlet end of the flow channel, whereby the membrane wall shear force of the suspension in laminar flow through the flow channel gradually and uniformly varies along the length of the flow channel from a maximum value at its inlet end to a minimum value at its outlet end. However, Solomon et al. device requires enormous membrane surfaces for blood plasma separation which appear not economically practical.

For the purposes of increasing the transmembrane pressure drop hopefully to catch a higher separation efficiency and a less concentration polarization effect, Fischel in U.S. Pat. No. 5,034,135, Schoendorfer in U.S. Pat. No. 5,194,145, Duff in U.S. Pat. No. 5,234,608, and Brown in U.S. Pat. No. 5,529,691 all disclose a blood separating system comprising high rotational velocity flow applying centrifugal forces aiming for added transmembrane pressure drop. During high centrifugal rotation, a portion of the cellular components may undesirably remain in the rotational device or inside pores of the filter membrane for a prolonged time and may subject to hemolysis, cellular damage or membrane clogging. For centrifugal-type separation processes, the local shear force for the cellular components of the blood concentrate fraction is the highest at about the periphery of the separation apparatus, such as a spinner-type device and the like. The requirement of a proper shear force at the outer-most region in a rotational separator apparently limits the size, and therefore the capacity, of the separation apparatus or the spinner.

Alternately, to create adequate local flow rate and subsequently local shear force in a plasmapheresis process, Duggins in U.S. Pat. No. 4,735,726 discloses a process for continuous plasmapheresis comprising conducting blood over a microporous membrane in a reciprocatory pulsatile flow pattern. The pulsatile flow is known to cause certain degrees of turbulence as the pulsatile flow rate changes constantly which may possibly cause cell damage and membrane clogging. Duggins discloses a damage-controlling method to compensate for the shortcomings of the pulsatile flow in a continuous plasmapheresis by reducing the transmembrane pressure difference to below zero during each forward and reverse flow. This additional equipment setup and control mechanism for repetitively reversing the transmembrane pressure difference makes this process less economically attractable.

There is an urgent clinical need to provide an efficient plasmapheresis process by minimizing the cellular damage while increasing the flow output. This may be achievable by controlling the local flow rate and local shear force of a filtration apparatus comprising a filter membrane with an orbital motion to minimize problems of undesired turbulence and concentration polarization in a conventional separating apparatus.

SUMMARY OF THE INVENTION

In general, it is an object of the present invention to provide a method and an improved apparatus for enhanced plasmapheresis. It is another object of the present invention to provide an improved separating apparatus for blood fractionation, for cell washing of blood autotransfusion, for bone marrow transfusion, for peripheral stem cell transfusion, and the like. It is a further object of the present invention to provide a filtration system and methods thereof comprising a fluid supply containing filtrate and particulate constituent.

Enhanced continuous plasmapheresis is accomplished by continually feeding a blood supply through a filtration chamber to effect separation of plasma components and cellular components. The blood passes in essentially parallel to the plane of the filtration membrane at flow rates sufficient to create shear stress across the membrane in the order of 10 to 2,000 dynes/cm$^2$, a preferred range being from about 100 to about 1,000 dynes/cm$^2$. The membrane has a pore size, pore shape, and cells affinity sufficient to allow the plasma components to pass therethrough but retain cellular components thereon. Generally pore sizes of from 0.2 to 1.0 microns are preferred for plasma or platelet separation. Transmembrane pressure of from about 10 mmHg to about 1,000 mmHg are employed to separate the blood into cellular components and plasma fractions. With assistance of the orbital motion of the membrane, the local flow rate and shear stress can be controlled, resulting in a narrower range of the transmembrane pressure that has lower hemolysis and lower plugging propensity.

In order to accomplish the enhanced plasmapheresis, a filtration system may comprise a filtration chamber having a hollow interior enclosed by a first plate, a second plate, and a flexible seal element between the first plate and the second plate, wherein the first plate is either essentially parallel to or at an acute angle to the second plate so as to form a chamber gap for the hollow interior. The filtration system further comprises a fluid supply means for supplying a fluid containing filtrate and particulate constituent; a means for directing the fluid supply into the hollow interior; and a filtrate collecting means for directing the filtrate passing through the filter membrane means to a collecting means and a particulate constituent collecting means for directing from the chamber gap a remaining constituent of the fluid supply out of the chamber. The second plate comprises filter membrane means for separating filtrate from the particulate constituent, and wherein the second plate is detachably coupled to a non-rotational drive structure that controls the second plate in an orbital motion in reference to a center axis of the first plate.

The term of "orbital motion" as used in the patent application refers to a motion that moves back and force between two points in a continuous manner, wherein the route of the forward movement may either partially overlap or not overlap the route of the backward movement. However, the "orbital motion" is different from "rotation" in this patent application. "Rotation" is defined as a movement in such a way that all particles follow circles with a common angular velocity about a common axis. (Webster's New Collegiate Dictionary, G & C Merriam Co. 1980).

In a preferred embodiment, a blood filtration apparatus may comprise a chamber having a hollow interior enclosed by a first plate, a second plate, and a flexible seal element between the first plate and the second plate, wherein the first plate is either essentially parallel to or at an acute angle to the second plate so as to form a chamber gap for the hollow interior; wherein said second plate comprising filter membrane means for separating plasma constituent from the blood, wherein the second plate is detachably coupled to a non-rotational drive structure that controls the second plate in an orbital motion in reference to a center axis of the first plate. The blood filtration apparatus further comprises means for directing a blood supply into the chamber gap; means for directing the plasma constituent passing through the filter membrane means to a collecting means; and means for directing from the chamber gap a remaining constituent of the blood out of the chamber.

In a still further embodiment, a blood filtration method for use in separating filtrate from blood supply comprises the steps of (a) feeding the blood supply into a chamber having a hollow interior enclosed by a first plate, a second plate, and a flexible seal element between the first plate and the second plate, wherein the first plate is either essentially parallel to the second plate or at an acute angle to the second plate so as to form a chamber gap for the hollow interior; said second plate comprising filter membrane means for separating filtrate constituent from the blood, wherein the second plate is detachably coupled to a non-rotational drive structure that controls the second plate in an orbital motion in reference to a center axis of the first plate; (b) initiating orbital motion of the second plate by the non-rotational drive structure to effect enhanced separation of filtrate from blood supply; (c) collecting the filtrate constituent passing through said filter membrane means; and (d) discharging a remaining constituent of the blood from the chamber gap out of the chamber. The blood supply may comprise at least one component selected from the group consisting of red blood cell, white blood cell, and platelet.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 4, what is shown is an embodiment of the enhanced separation process employing a separation chamber comprising a filter membrane under an orbital motion. The enhanced separation process is particularly applicable for plasmapheresis and other medical applications, such as for blood fractionation, for blood autotransfusion, for bone marrow transfusion, for peripheral stem cell transfusion, and the like.

Figure 1:
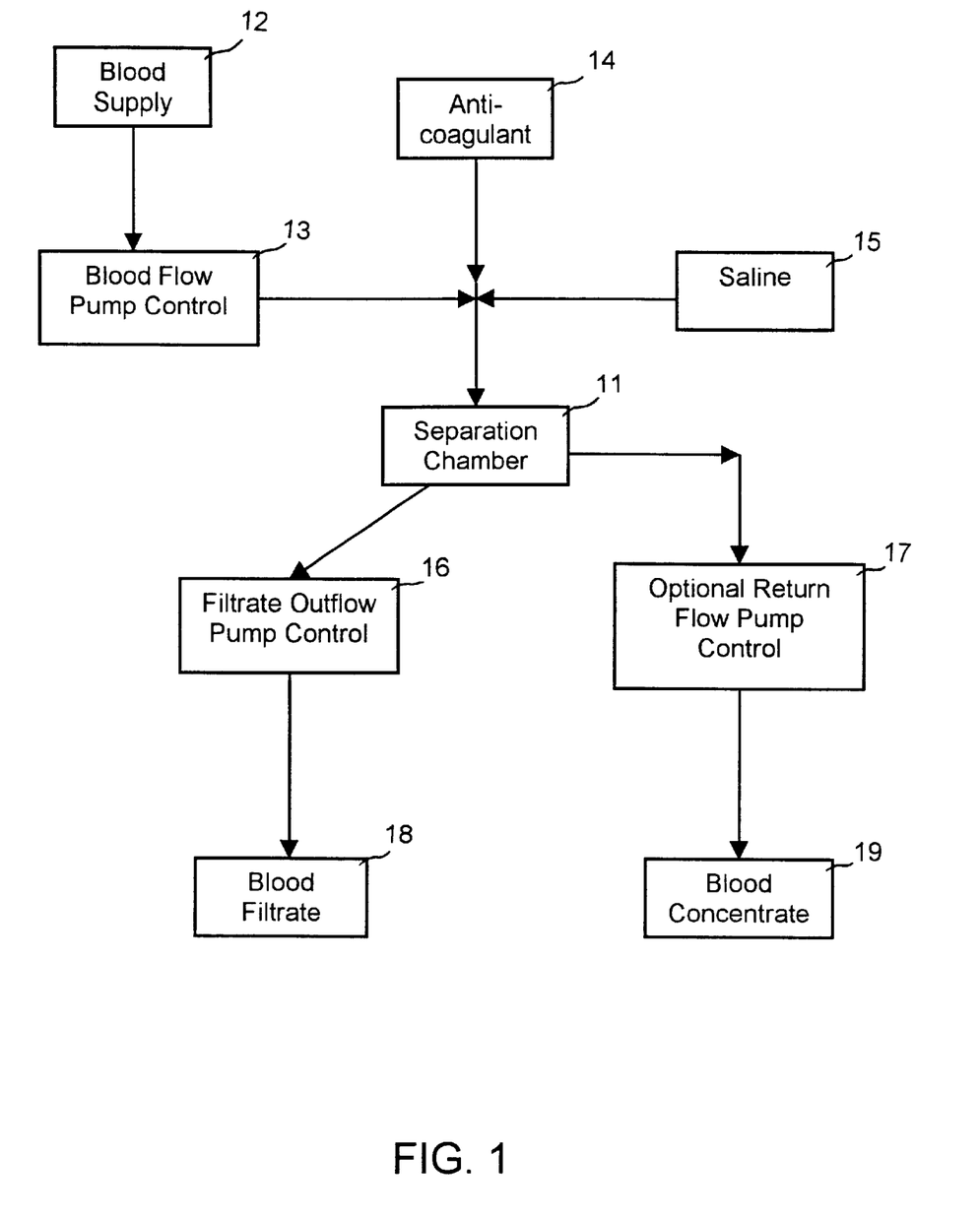
FIG. 1 is a schematic diagram of an enhanced blood separation process employing a separation chamber comprising a filter membrane under an orbital motion of the present invention.

FIG. 1 shows a schematic diagram of an enhanced blood separation process employing a separation chamber comprising a filter membrane under an orbital motion of the present invention. The blood supply 12 to the apparatus 11 may comprise fresh whole blood, thawed blood, or partially fractionated blood. The blood supply is fed to the separation chamber 11 via a blood flow pump control 13 or other means for directing a blood into the separation chamber 11. To maintain the blood supply from coagulation, anticoagulant 14 may optionally be added into the blood supply at an appropriate point of the blood supply feeding line. Similarly, saline 15 may optionally be added during the blood-feeding step. A positive pressure is generally maintained during the plasmapheresis of the present invention. The pressure difference across the membrane is preferably in the range of 10 to 1000 mm of mercury. The pressure difference is controlled by the flow rates of the blood flow pump control 13, the filtrate outflow pump control 16 and/or the return flow pump control 17.

Blood filtrate 18 is collected from the opposite side of the filter membrane, wherein the filtrate collecting means is completely isolated from communication with the blood supply. The filtrate is collected from the separation chamber 11 via a filtrate outflow pump control 16 or other means for directing the plasma constituent passing through the filter membrane. Blood concentrate 19 or the cellular constituent portion is withdrawn from the separation chamber 11 via an optional return flow pump control 17 or other means for directing a remaining constituent of the blood out of the chamber.

The pressure drops across the filter membrane can be adjusted by manually adjusting one or more of the flow pump controls 13, 16, and 17, or by providing automatic adjusting mechanisms. The pressure drop may be measured by an optional differential pressure indicator and/or controlled by the automated adjusting mechanisms.

Figure 2:
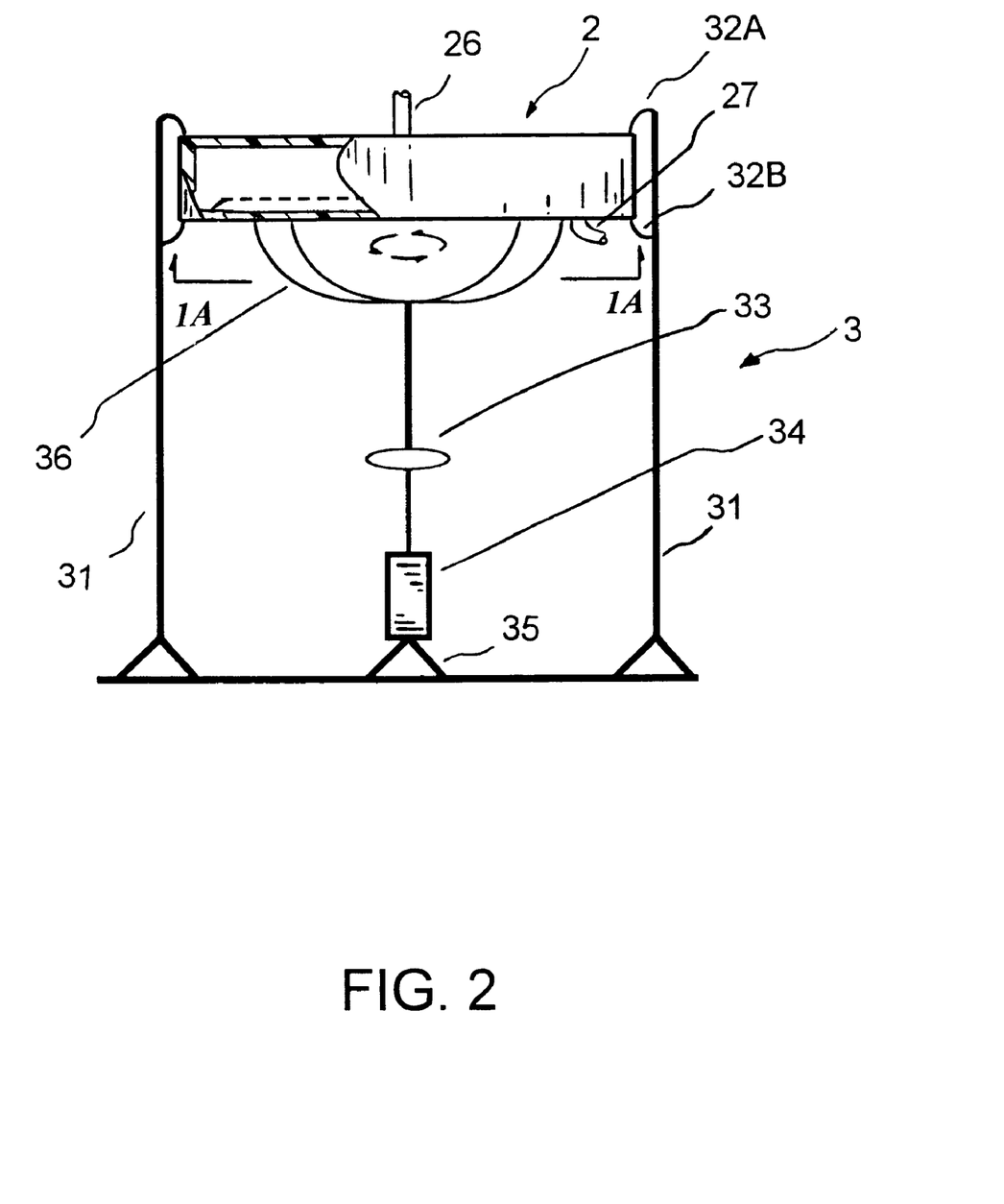
FIG. 2 is an illustrative setup of an enhanced blood separation process employing a separation chamber comprising a filter membrane under an orbital motion.

FIG. 2 shows an illustrative setup of an enhanced blood separation process employing a separation chamber comprising a filter membrane under an orbital motion. A plasmapheresis setup comprises a supporting installation 3 that can be rolled away or placed at any convenient location and a removable blood filtration apparatus 2. The supporting installation 3 comprises a plurality of supporting poles 31 and a rotatable means 34 for generating orbital motion through a non-rotational structure 33 to the blood filtration apparatus 2. The rotatable means 34 may be selected from the group consisting of a rotatable magnetic motor, a rotatable mechanical motor and the like, wherein the rotatable means 34 is firmly attached to the supporting installation 3 via an attachment 35.

Each supporting pole 31 has a couple of grabbing pins 32A, 32B for securely and firmly holding the blood filtration apparatus 2 in place when the removable blood filtration apparatus 2 is placed into the supporting installation 3. The grabbing pins 32A, 32B are generally equipped with a spring-like mechanism for releasing the blood filtration apparatus 2 when the apparatus needs to be removed from the supporting installation 3. The supporting poles 31 are so designed that the blood filtration apparatus 2 when placed into slots of the grabbing pins 32A, 32B is always at a level without undue vibration caused by the rotatable means 34.

The separation chamber 4 may be installed horizontally, vertically or at any angle. However, for space-saving purposes and taking into consideration of gravity, a preferred setup is a horizontal separation chamber detachably coupled to a vertical non-rotational structure 33.

In an illustrative example, a mechanical motor is used as the rotatable means 34. One end of an elongate shaft is secured to an axis of the mechanical motor while the end of the elongate shaft has a cam. The non-rotational drive structure 33 intimately contacts is an edge of the cam and is indirectly coupled to the rotatable means 34 for generating orbital motion to the second plate. Therefore, when the cam rotates, the non-rotational drive structure 33 moves in an orbital motion. The frequency of the orbital motion is related to the rotational frequency of the motor while the off-center distance of the orbital motion is related to the diameter and shape of the cam.

Figure 3:
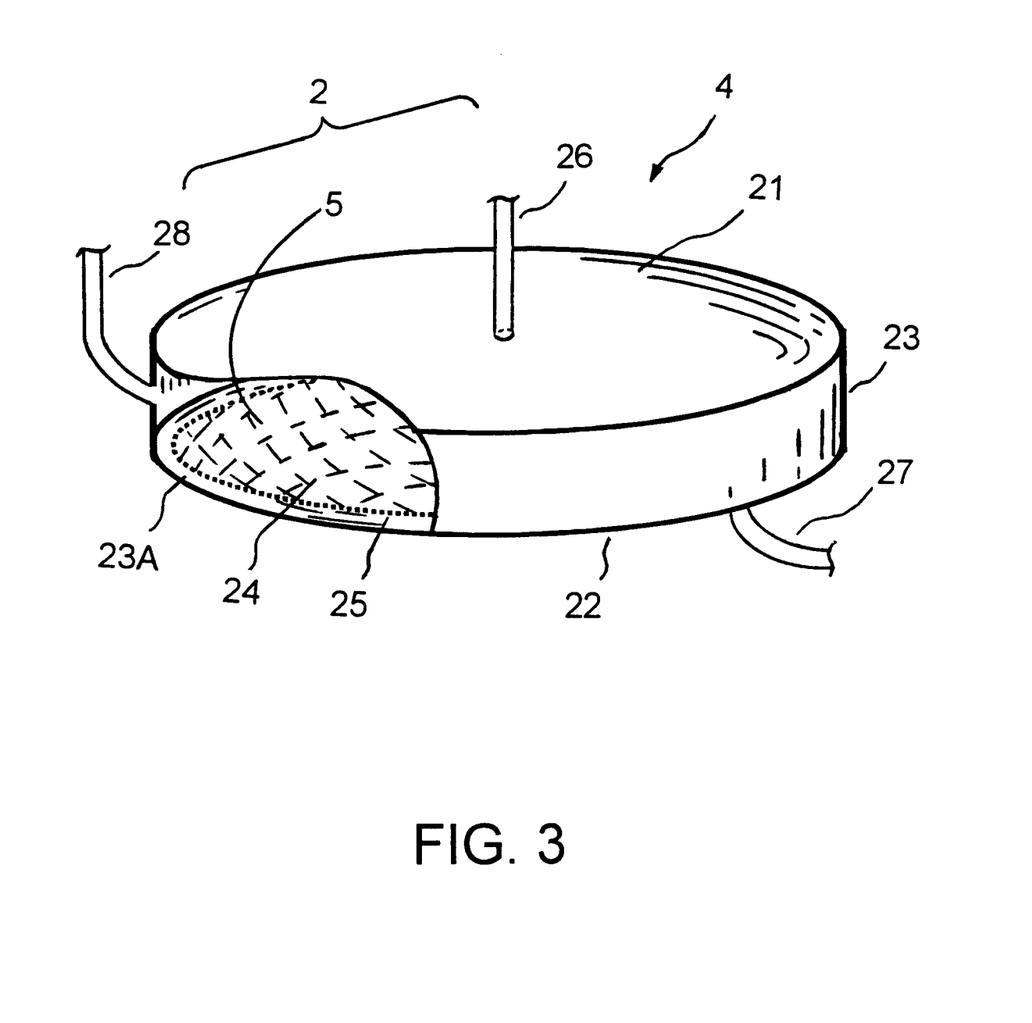
FIG. 3 is a perspective view of the blood filtration apparatus comprising the separation chamber having a filter membrane.

FIG. 3 shows a perspective view of the blood filtration apparatus 2 comprising a separation chamber 4 having a filter membrane 24. The blood filtration apparatus 2 comprises a separation chamber 4, a means 26 for directing a blood into the chamber gap, a means 27 for directing the plasma constituent passing through the filter membrane means to a collecting means, and a means 28 for directing from the chamber gap a remaining constituent of the blood out of the separation chamber 4.

The separation chamber 4 comprises a hollow interior 5 enclosed by a first plate 21, a second plate 22, and a flexible seal element 23 between the first plate 21 and the second plate 22, wherein the first plate 21 is either essentially parallel to or at an acute angle to the second plate 22 so as to form a chamber gap for the hollow interior 5. The second plate 22 comprises filter membrane means 24 for separating plasma constituent from the blood, wherein the second plate 22 is detachably coupled to a non-rotational drive structure 33 that controls the second plate 22 in an orbital motion in reference to a center axis of the first plate 21. The chamber 4 is generally detachable from the non-rotational drive structure 33.

The location of the means 26 for directing a blood into the chamber gap may be selected from the group consisting of at about a center of the first plate, at about periphery of the first plate, and at about a corner of the first plate. Similarly, the location of the means 27 for directing the plasma constituent to a collecting means may be selected from the group consisting of at about periphery of the second plate, at about a center of the second plate, and at about a corner of the second plate. The above-mentioned location is determined by the application, the design and the construction of the blood filtration apparatus. In a preferred setup for a horizontal separation chamber 4, the means 26 for directing a blood supply 12 into the chamber gap may be from the top of the separation chamber downward toward the filter membrane 24 or from the bottom of the separation chamber upward toward the filter membrane. To maintain the cellular components in a suspension mode by gravity, the means for blood supply upward toward the separation membrane may be preferred.

In one preferred embodiment, the acute angle between the first plate and the second plate is in the range of 1 degree to 40 degrees so that the concentration polarization effect is minimized. The acute angle may preferably be in the range of 1 degree to 15 degrees. The acute angle may be measured from one side of the two plates to another side of the plates, from the center to the periphery of the plates or in other arbitrary manner.

The flexible seal element 23, 23A may be selected from the group consisting of silicone, polyurethane, latex, Nylon, polyvinyl chloride, polyimide, polycarbonate, polyacrylate, polymethacrylate, polystyrene, polyethylene, polypropylene, their mixture, and their copolymer. The flexible seal element of the present invention refers to a seal material that is flexible and fluid-tight so that the second plate 22 can move in an orbital motion in reference to a center axis of the first plate 21.

The filter membrane means 24 for separating the plasma constituent from the blood may be selected from the group consisting of nylon membrane, polycarbonate membrane, polysulfone membrane, oval pore membrane, microfabricated membrane, tract-edged membrane, a combination of the above and the like. In a preferred embodiment, the filter membrane means 24 is partially attached to the second plate 22 at periphery 25 of the second plate 22 so that a space below the filter membrane 24 has no fluid communication with the chamber interior 5 except through the membrane 24 itself. The periphery 25 of the second plate 22 is joined with the flexible seal element 23 by a flexible seal material 23A so that the two plates 21, 22 can move orbitally, but not rotate, relative to each other.

In order to maximize the separation efficiency, the separation chamber can be in a round shape or in other appropriate shape to take advantages of the orbital motion or movement of the second plate. The filter membrane can also be in a round shape or in other appropriate shape. The filter membrane and its properties for separating blood supply or other solute-containing fluid are well known to one of ordinary skill in the art.

The interior surface of the second plate 22 facing the downstream side of the filter membrane 24 may be ribbed and/or studded. It is adapted for allowing the plasma constituent to pass through the filter membrane means onto the spaces between the ribs and/or studs of the interior surface and subsequently to the collecting means 27. The pattern of ribs may be selected from the group consisting of concentric circular ribs, hexagonal ribs, square ribs and the like. The studs can be in any fashion on the interior surface of the second plate. In an alternate embodiment, the middle portion of the filter membrane 24 is detached from the interior surface of the second plate 22. A vibration means for causing the middle portion of the membrane to vibrate so as to minimize membrane clogging during blood filtration may be optionally provided. The vibration means may comprise an electromagnetic mechanism.

To effect the optimal plasma filtration, the filter membrane usually has pores of a size on the order of 0.2 to 1.0 $\mu$m. A preferred range of pore size is around 0.4 to 0.6 $\mu$m. The selection of pore size may vary with the goal of a particular separation process. As exemplary of membranes having the preferred properties for plasmapheresis with an orbital movement are HT 450 polysulfone membrane commercially available from Gelman Sciences, Inc., the polyester and polycarbonate membranes commercially available from Nuclepore Corporation.

The chamber gap may be between 0.001 to 0.1 inch for generating optimal local flow rate and local shear force for plasma filtration process. A preferred range of chamber gap is about 0.03 to 0.06 inch. The optimal shear force for enhanced filtration process of the present invention is a function of a combination of the chamber gap, the flow rates of the fluid supply and the outflow filtrate, and the orbital motion characteristics, wherein the orbital motion characteristics may comprise the orbiting frequency, orbiting distance, and orbiting manners. A preferred range of shear force is around 100 to 1,000 dynes/cm$^2$. means may comprise an electromagnetic mechanism.

To effect the optimal plasma filtration, the filter membrane usually has pores of a size on the order of 0.2 to 1.0 $\mu$m. A preferred range of pore size is around 0.4 to 0.6 $\mu$m. The selection of pore size may vary with the goal of a particular separation process. As exemplary of membranes having the preferred properties for plasmapheresis with an orbital movement are HT 450 polysulfone membrane commercially available from Gelman Sciences, Inc., the polyester and polycarbonate membranes commercially available from Nuclepore Corporation.

The chamber gap may be between 0.001 to 0.1 inch for generating optimal local flow rate and local shear force for plasma filtration process. A preferred range of chamber gap is about 0.03 to 0.06 inch. The optimal shear force for enhanced filtration process of the present invention is a function of a combination of the chamber gap, the flow rates of the fluid supply and the outflow filtrate, and the orbital motion characteristics, wherein the orbital motion characteristics may comprise the orbiting frequency, orbiting distance, and orbiting manners. A preferred range of shear force is around 100 to 1,000 dynes/cm$^2$.

Figure 4:
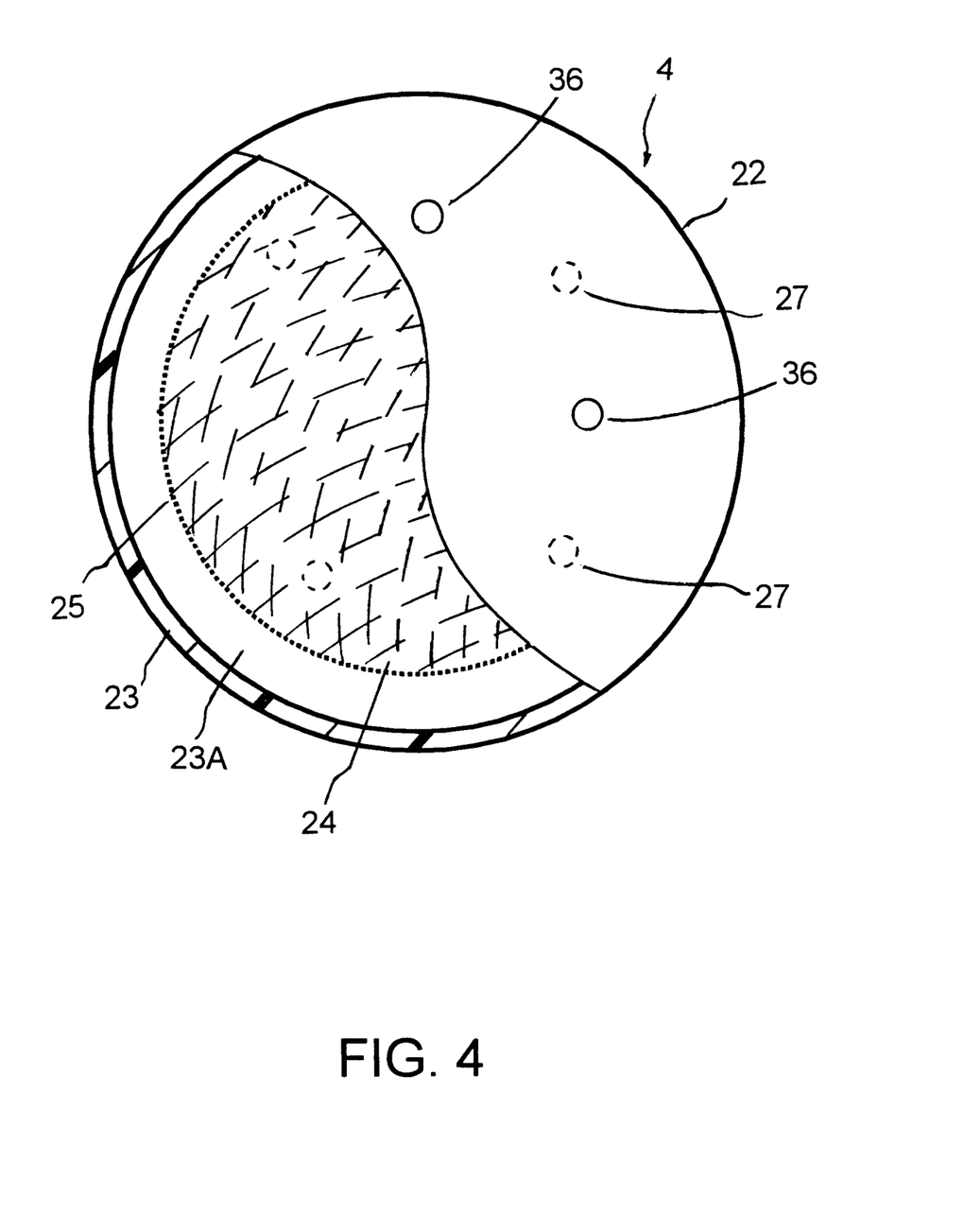
FIG. 4 is a bottom view of the separation chamber for section 1A—1A of FIG. 2

FIG. 4 shows a bottom view of the separation chamber 4 from section 1A—1A of FIG. 2. A plurality of coupling elements 36 is part of the non-rotational drive structure 33, wherein the coupling element 36 is detachably coupled to an exterior side of the second plate 22 of the separation chamber 4 for causing the second plate 22 to have an orbital motion in reference to a center axis of the first plate 21. The orbital motion or movement may be selected from the group consisting of clockwise movement, counterclockwise movement and a combination of the above. The off-center orbital motion or movement is generally within a range of 0.001 to 1.0 inch distance. More preferably, the off-center orbital motion is in the range of about 0.05 to 0.5 inch distance. In a further embodiment, the orbital motion may be at a frequency within a range of 500 to 50,000 cycles per minute. The frequency of the orbital motion is preferred in the range of 1,000 to 20,000 cycles per minute. The pattern of the orbital motion or movement may be selected from the group consisting of circular shape movement, oval shape movement, peanut shape movement, pear shape movement, and irregular shape movement.

For application, a blood filtration method for use in separating filtrate from blood supply comprises the steps of (a) feeding blood supply into a separation chamber comprising filter membrane means for separating filtrate constituent from the blood; (b) initiating orbital motion of the filter membrane to effect enhanced separation of filtrate from blood supply; (c) collecting the filtrate constituent passing through the filter membrane; and (d) discharging a remaining constituent of the blood out of the separation chamber and/or returning to the donor.

From the foregoing description, it should now be appreciated that an enhanced plasmapheresis apparatus and methods for using same comprising a filter membrane under an orbital motion that has optimal local shear forces and maximum plasma flow output have been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A blood filtration apparatus comprising:
   a chamber having a hollow interior enclosed by a first plate, a second plates and a flexible seal element between the first plate and the second plate, wherein the first plate is either essentially parallel to or at an acute angle to the second plate so as to form a chamber gap for the hollow interior;
   means for directing blood into the chamber gap;
   a non-rotational drive structure;
   said second plate comprising filter membrane means for separating plasma constituent from the blood, wherein the second plate is detachably coupled to said non-rotational drive structure that controls the second plate in an orbital motion in reference to a center axis of the first plate;
   a collecting means;
   means for directing the plasma constituent passing through said filter membrane means to said collecting means; and
   means for directing from the chamber gap a remaining constituent of the blood out of the chamber.

2. The blood filtration apparatus as in claim 1, wherein the first plate is at an acute angle to the second plate and wherein the acute angle is in the range of 1 degree to 40 degrees.

3. The blood filtration apparatus as in claim 1, wherein the flexible seal element is selected from the group consisting of silicone, polyurethane, latex, Nylon, polyvinyl chloride, polyimide, polycarbonate, polyacrylate, polymethacrylate, polystyrene, polyethylene, polypropylene, mixture thereof, and copolymer thereof.

4. The blood filtration apparatus as in claim 1, wherein the chamber gap is between 0.001 to 0.1 inch.

5. The blood filtration apparatus as in claim 1, wherein the orbital motion is selected from the group consisting of clockwise movement, counter-clockwise movement and combination thereof.

6. The blood filtration apparatus as in claim 1, wherein the filter membrane means has pores of a size on the order of 0.2 to 1.0 $\mu$m.

7. The blood filtration apparatus as in claim 1 further comprising an off-center orbital motion, wherein the off-center orbital motion is within a range of 0.001 to 1.0 inch.

8. The blood filtration apparatus as in claim 1, wherein the orbital motion is at a frequency within a range of 500 to 50,000 cycles per minute.

9. The blood filtration apparatus as in claim 1, wherein the orbital motion is selected from the group consisting of circular shape movement, oval shape movement, peanut shape movement, pear shape movement, and irregular shape movement.

10. The blood filtration apparatus as in claim 1, wherein pressure within the means for directing blood into the chamber gap is higher than pressure within the means for directing the plasma constituent passing through said filter membrane means to said collecting means.

11. The blood filtration apparatus as in claim 1, wherein the means for directing blood into the chamber gap is located either at about a center of the first plate or at about a periphery of the first plate.

12. The blood filtration apparatus as in claim 1, wherein the means for directing the plasma constituent to said collecting means is located either at about a periphery of the second plate or at about a center of the second plate.

13. The blood filtration apparatus as in claim 12, wherein an interior surface of the second plate is ribbed and adapted for allowing the plasma constituent to pass through the filter membrane means to the collecting means.

14. The blood filtration apparatus as in claim 1, wherein the filter membrane means for separating the plasma constituent from the blood is selected from the group consisting of nylon membrane, polycarbonate membrane, polysulfone membrane, oval pore membrane, micro-fabricated membrane, tract-edged membrane and combination thereof.

15. The blood filtration apparatus as in claim 1, wherein the filter membrane means is partially attached to the second plate at a periphery of the second plate.

16. The blood filtration apparatus as in claim 1 further comprising a rotatable means, wherein the non-rotational drive structure is coupled to said rotatable means for generating orbital motion to the second plate.

17. The blood filtration apparatus as in claim 16, wherein the rotatable means is selected from the group consisting of rotatable magnetic motor and rotatable mechanical motor.

18. A blood filtration method for use in separating filtrate from blood supply comprising the steps of:
   (a) feeding blood supply into a chamber having a hollow interior enclosed by a first plate, a second plate, and a flexible seal element between the first plate and the second plate, wherein the first plate is essentially parallel to the second plate so as to form a chamber gap for the hollow interior; said second plate comprising filter membrane means for separating filtrate constituent from the blood, wherein the second plate is detachably coupled to a non-rotational drive structure that controls the second plate in an orbital motion in reference to a center axis of the first plate;
   (b) initiating orbital motion of the second plate by the non-rotational drive structure to effect enhanced separation of filtrate from blood supply;
   (c) collecting the filtrate constituent passing through said filter membrane means; and
   (d) discharging a remaining constituent of the blood from the chamber gap out of the chamber.

19. The blood filtration method as in claim 18, wherein the blood supply comprises at least one component selected from the group consisting of red blood cell, white blood cell, and platelet.

20. A filtration system comprising:
   fluid supply means for supplying a fluid containing filtrate and particulate constituent;
   a filtration chamber having a hollow interior enclosed by a first plate, a second plate, and a flexible seal element between the fist plate and the second plate, wherein the first plate is essentially parallel to or at an acute angle to the second plate so as to form a chamber gap for the hollow interior;
   means for directing the fluid supply into the hollow interior;
   a non-rotational drive structure;
   said second plate comprising filter membrane means for separating filtrate from the particulate constituent, wherein the second plate is detachably coupled to said non-rotational drive structure that controls the second plate in an orbital motion in reference to a center axis of the first plate;

a collecting means; filtrate collecting means for directing the filtrate passing through said filter membrane means to said collecting means; and particulate constituent collecting means for directing from the chamber gap a remaining constituent of the fluid supply out of the chamber.

* * * * *